United States Patent [19]

Sipos

[11] 4,079,125
[45] Mar. 14, 1978

[54] PREPARATION OF ENTERIC COATED DIGESTIVE ENZYME COMPOSITIONS

[75] Inventor: Tibor Sipos, Lebanon, N.J.

[73] Assignee: Johnson & Johnson, New Brunswick, N.J.

[21] Appl. No.: 744,902

[22] Filed: Nov. 26, 1976

Related U.S. Application Data

[63] Continuation-in-part of Ser. No. 585,621, Jun. 10, 1975, abandoned.

[51] Int. Cl.² ........................ A61K 9/32; A61K 9/58; A61K 37/48
[52] U.S. Cl. ...................................... 424/32; 424/31; 424/35; 424/78; 424/80; 424/94
[58] Field of Search .................... 424/94, 78, 80, 31, 424/32, 35

[56] References Cited

U.S. PATENT DOCUMENTS

| | | | |
|---|---|---|---|
| 3,691,090 | 9/1972 | Kitajima et al. | 424/94 |
| 3,789,117 | 1/1974 | Tsujino | 424/94 |
| 3,859,228 | 1/1975 | Morishita et al. | 424/94 |

Primary Examiner—Sam Rosen

[57] ABSTRACT

Improved enteric coated digestive enzyme-containing compositions which are capable of withstanding hours of exposure to gastric fluids while protecting the biological activity of the enzymes and thereafter releasing the digestive enzymes in their biologically active state within 5 to 30 minutes after being exposed to intestinal fluids, these compositions comprising (a) an enzyme concentrate in (b) a binder system comprising at least about 0.5 wt. %, preferably about 1 to about 10 wt. % (based on the weight of the binder system plus enzymes) of (i) a binder, preferably selected from the group consisting of polyvinylpyrrolidone, microcrystalline cellulose (Avicel), cellulose acetate phthalate, methylcellulose and alginic acid, and preferably (ii) from about 0.1 to about 10 wt. % of a stabilizer, preferably selected from the group consisting of calcium carbonate, polyvinylpyrrolidone, cellulose acetate phthalate, methylcellulose, alginic acid, starch and modified starches, e.g., carboxymethyl starch (Primojel); and (c) from about 0.1% to about 30 wt. %, based on the weight of the total composite (enzyme plus binder system plus disintegrant) of a disintegrant, preferably selected from the group consisting of citric acid, sodium carbonate, sodium bicarbonate, calcium carbonate and other suitable carbonates, alginic acid, starch and modified starches, e.g., carboxymethyl starch (Primojel) are prepared by a process in which the presence of water is avoided and which includes the step of blending enzyme, binder and disintegrant in the presence of a selected inert solvent as well as the subsequent coating of the resulting enzyme/binder/disintegrant composite with from about 2.5% to about 10% by weight, based on the weight of the enzyme/binder/disintegrant composite, of a gastric juice insoluble, intestinal juice soluble, non-porous, pharmaceutically acceptable enteric coating polymer.

30 Claims, No Drawings

PREPARATION OF ENTERIC COATED DIGESTIVE ENZYME COMPOSITIONS

CROSS REFERENCE TO RELATED APPLICATIONS

This is a continuation-in-part of my copending application, Ser. No. 585,621, filed June 10, 1975, now abandoned.

BACKGROUND OF THE INVENTION

1. Field of the Invention

This invention relates to enzyme compositions for ingestion by a mammal having a digestive disorder which is caused by an enzyme deficiency or which, in any event, can be alleviated by enzyme supplements. More particularly, the invention relates to improved enteric coated enzyme-containing compositions for ingestion by a mammal, as well as to methods for making such a composition.

2. Description of the Prior Art

It is well documented in the literature that exogenously administered pancreatic enzymes from animal sources can remedy the enzyme deficiency caused by various diseased states of the pancreas, e.g., pancreatitis, pancreatectomy, cystic fibrosis, etc. Fewer data exist for enzymes from plant and microbial sources.

Pancreatic enzymes are active under near neutral and slightly alkaline conditions. Under gastric conditions, i.e., in the presence of acid and pepsin, most of the enzymes are irreversibly inactivated with resulting loss of biological activity. Therefore, it is imperative that the exogenously administered enzymes be protected against gastric inactivation and remain intact during their transit through the stomach into the duodenum.

While the transit of the enzymes intact through the stomach is essential, it is another requirement for maximum efficacy that the enzymes be released in the duodenum within 5 to 30 minutes, since digestion by pancreatic enzymes and absorption of the metabolites take place primarily in the upper segment of the intestine, i.e., duodenum and upper part of the jejunum.

The normal pancreas, in reponse to food stimulation, gradually releases the digestive exzymes, mostly in their inactive precursor form, into the duodenum. Some of the released zymogens (inactive precursors) are first activated by enterokinase to form active enzymes, e.g., trypsin from trypsinogen. The newly activated trypsin in turn generates more active enzymes in the duodenum by an autocatalytic mechanism. Simultaneously, the activated enzymes are thoroughly mixed with the arriving food from the stomach, and digestion ensues. This process takes place as long as food is pumped from the stomach into the duodenum.

Pancreatic enzymes have been used for the past seventy years to treat various digestive disorders. The early clinical results were variable. With time it became apparent that some of the poor clinical responses were due to gastric inactivation of the exogenously administered enzymes. A revived interest in enzyme-containing digestive aids occurred in the late 1950's and early 1960's, with the development of acid stable enteric coatings. Thus, it was believed that the detrimental effects of gastric acidity on the enzymes could be avoided by the use of such enteric coatings, and more effective enzyme therapy thus made possible. A great variety of enteric coated enzyme-containing digestive aids were marketed in this period. However, most of these products contained low levels of active enzymes, often too low to effectively treat many enzyme deficiency-related conditions. Many of these products were particularly deficient in lipase.

Moreover, the coatings generally failed to protect the enzymes against gastric inactivation or to release them in an activatable state in the duodenum. Thus, most were permeable to gastric acid and many failed to disintegrate in the duodenum under neutral conditions within a reasonable time, from the point of view of being available in proper concentration in active form at the time when food which has passed through the stomach is present in the duodenum and upper jejunum.

Because of these known defects in the coatings as well as the low levels of enzyme activities of prior art digestive enzyme-containing compositions, it has long remained a desired goal to develop a highly active enzyme-containing digestive aid composition that would prevent gastric acid and pepsin inactivation of the enzymes upon passage through the stomach, and, after transit from the stomach into the duodenum, would release the enzymes in a reproducible, i.e., predictable, manner within minutes in their biologically active state.

In a pancreatic deficient state the normal physiological conditions of digestion (i.e., gradual release of pancreatic zymogens into the duodenum, their activation by enterokinase and their even mixing with the incoming food from the stomach) in the duodenum are absent or greatly impaired. Exogenous administration of the enzymes in large tablets can aggravate the already existing abnormal physiological state because large amounts of enzymes may be released into small, concentrated areas. This in turn could result in irritation and damage to the intestinal lining. Furthermore, any asynchrony that may exist between the arrival of food and of the tablets from the stomach into the duodenum will further reduce the possibility that normal digestion can take place under this condition. A tablet can arrive in the duodenum too early or too late with respect to arrival of the food. This results in unpredictable response and poor digestion.

As can be seen from the foregoing, the desiderata for a successful, highly acceptable digestive enzyme composition, which have not heretofore been satisfactorily provided by any one product, include: (1) providing a properly enteric coated composition which enables delivery of the exogenously administered enzymes intact through the stomach into the duodenum; (2) ensuring the release of the protected enzymes, in a biologically active state, into the duodenum within minutes after the passage of the compositions from the stomach into the duodenum by providing an enteric coating which will promptly dissolve in intestinal juices, and controlling the chemical composition, physical form and size of the digestive enzyme composition to promote rapid disintegration upon dissolution of the enteric coating; and (3) recreating the physiological conditions for digestion that exist in the duodenum with a normal functioning pancreas, by (a) providing the composition in small unit size form to promote even mixing thereof with the food in the stomach so that the enzymes are gradually released into the duodenum and are uniformly dispersed throughout the food arriving from the stomach, and (b) assuring that sufficient activators such as co-lipase are present to provide for the patient maximum benefit from his own naturally produced enzymes as well as those that are administered exogenously.

SUMMARY OF THE INVENTION

The present invention provides compositions, as well as methods for their preparation and use, that promote the delivery in a reproducible manner into the upper intestine, in a bio-available form, of exogenously administered digestive enzymes, as well as their release in a controlled, biologically acceptable manner. By virtue of this invention, a highly effective system is provided that greatly improves the nutritional and psychological well-being of enzyme deficient patients. With the regular use of this system, food digestion is aided. In addition, maldigestion due to enzyme deficiency as well as bacterial fermentation of undigested food in the lower intestine are prevented.

The compositions of the present invention comprise an enzyme concentrate in a binder selected from the group consisting of polyvinylpyrrolidone, microcrystalline cellulose, cellulose acetate phthalate, methylcellulose and alginic acid; and from zero to about 10 wt. % of a stabilizer selected from the group consisting of calcium carbonate, polyvinylpyrrolidone, cellulose acetate phthalate, methylcellulose, starch and modified starches and alginic acid; and from about 0.1% to about 30 wt. %, based on the total weight of the composite, of a disintegrant selected from the group consisting of citric acid, sodium carbonate, sodium bicarbonate, calcium carbonate, starch and modified starches, and alginic acid; the foregoing enzyme/binder/disintegrant composite being coated with from about 2.5% to about 10% by weight, based on the weight of the enzyme/binder/disintegrant composite, of a non-porous, pharmaceutically acceptable enteric coating polymer, whereby to provide an enteric coating which is insoluble in the pH range of from about 1.5 to about 5 normally existing in mammalian gastric fluids, but soluble at a pH of from about 6 to about 9, the normal pH range for mammalian intestinal fluids, so that said finished composition is capable of withstanding at least about one hour, preferably two hours, of exposure to mammalian gastric conditions, but will dissolve within about 5 to about 30 minutes in intestinal juices of mammals.

In one preferred embodiment, the present invention provides compositions which comprise a pancreatic enzyme mixture, each milligram of which contains at least about 75 N.F.* units of protease, at least about 75 N.F. units of amylase, at least about 10 N.F. units of lipase, preferably at least about 5 International Units (IU) of ribonuclease, and an effective amount of colipase in an enteric coated composition as described in the preceding paragraph.

*National Formulary, see Vol. VIII, P 514 et. seq. and the Supplement thereto, in particular the Second Supplement, pp. 1076-7, and the Fourth Supplement, pp. 1134 et. seq.

In accordance with a preferred feature of the present invention, the enteric coated enzyme compositions are provided in the form of "small beads", spherical particles having diameters in the preferred range of from about 8 to about 14 mesh. In theory, the smallest beads give the best distribution of enzymes in the food. However, extremely small beads are more difficult to form since they require an extremely finely powdered enzyme to form true spheres, whereas excessive milling of the enzyme powder irreversibly inactivates some of the enzymes. Extremely small enzyme beads also require a larger percentage of enteric coating due to the greater surface area. Therefore, although smaller than 14 mesh and larger than 8 mesh beads are suitable, the most practical size range is 8 to 14 mesh. Particularly preferred are beads in the 10 to 12 mesh range. As used herein, the expression 8 mesh means that the bead will be caught on a screen having a U.S. Series designation of 8 (which has square sieve openings of 2.38 mm), but pass through a screen having larger openings. Correspondingly, 14 mesh beads are caught on a screen having a U.S. series designation 14 (or openings of 1.68 mm), but pass through a screen having larger openings. For convenience of administration to the patient, these beads may be provided in gastric juice soluble capsules. Each capsule may suitably contain from about 250 to about 600 mg. of beads, preferably from about 425 to about 475 mg.

As an alternative, the more commonly used tablet form may be employed. In this event, however, it is preferred to limit the size of the coated tablet to the smallest feasible size in order to enhance the uniformity of distribution of the compositions of the present invention within the food passing from the stomach into the duodenum. Another advantage of employing a large number of smaller tablets is that inactivation of the enzymes in one tablet in the stomach due to an inadvertent flaw in the enteric coating will result in the loss of only a relatively small percentage of the total enzyme administered. For convenience, these tablets are preferably also administered in gastric juice soluble capsules, each capsule typically containing a plurality of small tablets.

In general, advantages of the bead form over the tablet form include provision of more uniform distribution of enteric coated enzyme composition throughout the food in the stomach due to the smaller size of the beads, the ability to readily obtain more uniform enteric coatings due to the spherical shape of the beads, and greater ease of disintegration in the intestines, since the poorer disintegration characteristics and loss of enzymatic activity caused by the pressures of compaction required to obtain a coherent tablet may be avoided in producing the spheres.

In accordance with another aspect of this invention, the compositions of the invention are prepared by a process which comprises granulating the enzyme or enzyme mixture, together with the binder and disintegrant, as well as the stabilizer, if present as a separate entity, in approximately 600-700 ml./kg. (of solids) of an inert solvent selected from the group consisting of isopropanol, methylene chloride, dioxane, tetrahydrofuran and acetone.

In a particularly preferred process in accordance with the present invention, the enzyme or enzyme mixture and disintegrant are mixed in the dry state, the binder (together with the stabilizer if any) is dissolved in a solvent as defined below to form a binder solution, and the composition is formed into beads having a diameter in the range of from about 8 to about 14 mesh by dusting said dry blend over nonpareil seeds tumbling and flowing in a coating pan, said seeds having been wetted with said binder solution, with periodic addition of binder solution to maintain the particles in a wetted but free-flowing state, until the seeds have been built to uniform spherical particles having diameters predominantly in said range of from about 8 to about 14 mesh.

DESCRIPTION OF THE PREFERRED EMBODIMENTS

The compositions of this invention include a digestive enzyme concentrate. In a presently preferred embodiment, they include the enzymes amylase, protease and lipase, together with co-lipase, and preferably also include ribonuclease. They also include at least one binder selected from the group consisting of cellulose acetate phthalate, polyvinylpyrrolidone, microcrystalline cellulose, alginic acid and methylcellulose and at least one disintegrant selected from the group consisting of sodium carbonate, sodium bicarbonate, citric acid, starches and modified starches (e.g., Primojel, Sta-Rx), microcrystalline cellulose, and alginic acid. As is known, when a carbonate is used as a disintegrant, it is used in combination with a mild acid, such as citric acid or tartaric acid. Preferably, they also include a separate stabilizer selected from the group consisting of calcium carbonate, polyvinylpyrrolidone, cellulose acetate phthalate, methylcellulose, starch and modified starches. It will be noted that the same material, e.g., polyvinylpyrrolidone, can act both as the binder and the stabilizer.

The principal active agents in the compositions of this invention, the enzymes, include such pancreatic enzymes as (I) the proteases, for example, Trypsin, E.C. (Enzyme Commission Number) 3.4.4.4; Chymotrypsin, E.C. 3,4,4,5; Chymotrypsin B, E.C. 3,4,4,6; Pancreatopeptidase E, E.C. 3.4.4.7; Carboxypeptidase A, E.C. 3.4.2.1; and Carboxypeptidase B, E.C. 3.4.2.2; (II) the lipases, for example, Glycerol ester hydrolase (Lipase), E.C. 3.1.1.3; Phospholipase $A_2$, E.C. 3.1.1.4; and Sterol ester hydrolase, E.C. 3.1.1.13; (III) the nucleases, for example, Ribonuclease, E.C. 2.7.7.16 and Deoxyribonuclease, E.C. 3.1.4.5; and the amylase, α-Amylase, E.C. 3.2.1.1. Among suitable digestive enzymes derived from plant sources are papain, E.C. 3.4.4.10; Chymopapain, E.C. 3.4.4.11; Bromelain, E.C. 3.4.4.c; Ficin, E.C. 3.4.4.12; and β-Amylase, E.C. 3.2.1.2. Suitable digestive enzymes derived from microbial sources include β-Galactosidase (Lactase), E.C. 3.2.1.23; Cellulase, E.C. 3.2.1.4; Subtilopeptidase A., E.C. 3.4.4.16; and Aspergillopeptidase A, E.C. 3.4.4.17.

Generally, the enzymes are available in powder or crystalline form, typically as concentrates of pancreatic enzymes (protease, amylase, lipase and, preferably, ribonuclease) derived from animal sources (hog, sheep and bovine). However, plant and microbial derived enzyme systems can also be used, if desired. Desirably, co-lipase is also included. To assure proper therapeutic effectiveness for pancreatic enzyme deficient patients, the initial enzyme activities per milligram should be at least those set forth above. In any event, for properly controlled therapy, it is important both to know the initial enzyme activities and to be able to predict the corresponding activity upon release in the intestinal tract. It should be understood that, as used herein, the term "enzyme" includes not only the already activated form but also the zymogen precursor which is capable of being transformed into the active form in mammalian intestinal fluid.

Suitable binders for granulation include polyvinylpyrrolidone (PVP) (Plasdone), microcrystalline cellulose (Avicel), cellulose acetate phthalate, and methylcellulose (Methocel). The binders are generally present in amounts of about 0.5% to about 10% by weight, preferably from about 1% to about 5% by weight. While greater percentages of binder could be used, I have found no advantage in exceeding 10% by weight.

Suitable stabilizers and disintegrants have been listed above and include, generally, those known to the art. The preferred weight ratio of disintegrants to enzymes is between about 2 and 15%, although between about 0.5% and 30% by weight may suitably be used.

The compositions of the invention may be prepared in tablet or bead form in accordance with the techniques described below. While each of these processes is analogous to processes employed heretofore in the preparation of other compositions, each is unique as applied to enzyme preparations. In particular, the discoveries that certain inert solvents may be used with the enzymes, as discussed below, as well as the particular parameters herein described in connection with the use of the solvents, are important features of the present invention.

(a) Granulation

In accordance with one aspect of the present invention, and as a preliminary step for both the production of tablets and the production of beads by segmentation or marumerization, the enzyme powder, the binder system and the disintegrant are blended together and granulated in an inert solvent as described in Remington's Practice of Pharmacy (RPP), XII pp. 445–449 (1961), and then extruded into segments through openings in the range of from about 0.5 to about 2 mm in diameter, preferably from about 0.8 to about 1.2 mm. These segments have a solvent content of about 47 to 55% by weight. Then the segments are further processed to their final form (e.g., tablet or bead) as described below.

In an alternative procedure of granulation, which has been employed for example with the enzyme blend of Example 6, the binder, e.g., polyvinylpyrrolidone, and the disintegrant, e.g., citric acid, are first dissolved in the inert solvent, e.g., isopropanol, and then slowly added to the enzyme mixture. Similarly to the previously described procedure, and as discussed below, the proper amount of solvent used for the granulation was found to be between about 600 and 700 ml/kg of enzyme blend. The advantage of this modified procedure over the previous one is that a more even distribution of the binder and the disintegrant are obtained. This in turn results in a more uniform product with faster disintegration and longer shelf-life (stability).

(b) Tablet Preparation

Tableting of the extruded and screened segments to form small tablets of convenient size, e.g., 4.8 mm. diameter and 4 mm. thickness, can be achieved by conventional tableting procedures at relatively low compression pressures and at temperatures of about 15° to 30° C. It has been observed that high compression pressures, which produce hard tablets having slow disintegration rates in intestinal juices, also result in elevated compression temperatures (i.e., 35° C and above). This causes a loss in biological activity. Preferably, the friability of the tablets should result in less than a 1% loss in 4 minutes under standard testing procedures. The hardness should be about 2 to 5 kilograms, preferably about 2.5 to 3.5.

In accordance with one aspect of the invention, the (uncoated) tablets are of relatively small size, having a diameter between about 2 and 7 mm., and a thickness between about 2 and 5 mm.

(c) Bead or Small Sphere Preparation

In accordance with another aspect of the invention, the segments are formed into beads having an average size in the range of from about 8 to about 14 mesh, preferably from about 10 to about 12 mesh.

One method of spheronization, or creation of beads, is to process the segments directly in a Marumerizer (see "A New Technique for the Production of Spherical Particles" by A. D. Reynolds, Manufacturing Chemist & Aerosol News, June 1970, p 40) for a period of from about 30 to about 75 seconds at a temperature of about 20° C. This procedure, while satisfactory, results in a wide range of particle sizes with a relatively low yield of the desired beads. In general, longer marumerization times result in more compact particles, which, by virtue of their greater compactness, require longer times for disintegration.

(d) Spherical Beads by a Non-Pareil Process

In accordance with yet another aspect of the invention, there is provided an alternative, preferred, procedure for the formation of small spheres or beads. This is based on the discovery that, under carefully controlled conditions as described below, larger spherical particles of digestive enzyme compositions can be obtained from small spherical particles (nonpareil seeds, typically sugar, having a mesh size generally in the range of from about 20 to about 32) by slowly dusting the enzyme/disintegrant composite over the tumbling and flowing nonpareil seeds wetted with the solvent containing the binder dissolved therein (binder solution) in a conventional coating pan, until the seeds build up in size to spherical particles having diameters in the range of from about 8 to about 14 mesh. In carrying out this process, the enzymes (see e.g., Example 9, Phase 1) are preblended with a disintegrant, preferably carboxymethyl starch (Primojel), in a Hobart mixer for 10 to 15 minutes. In a separate container, the binder/stabilizer, e.g., polyvinylpyrrolidone (PVP), blend is dissolved in 725 ml of a solvent, preferably isopropanol per kilogram of blend. The nonpareil sugar seeds are prewetted with the isopropyl alcohol-PVP solution (the degree of wetness being sufficient to promote adhesion of enzyme disintegrant mixture to the wetted sugar particles but not so great as to promote agglomeration of the beads), after which the preblended mixture of pancreatic enzymes and disintegrant is slowly sprinkled over the tumbling nonpareil sugar seeds in a conventional coating pan (e.g., as available from the Manesty Co.). The sequence of the above steps is repeated until the seeds are built up into beads of the desired sizes.

The above procedure results in high yields of uniform particle size, approximately 90% of the particles being within the range of 8 to 12 mesh, with the preservation of 90 to 95% of the biological activity. By comparison, during a conventional tableting operation under the conditions of the present invention, only about 70 to 90% of the biological activity is generally preserved.

e. Solvent

The solvent serves as the wetting agent. The term "inert solvent" as used herein means that the solvent does not have a deleterious effect on the biological activity of the enzymes nor adversely react with any other component of the composition of this invention.

Suitable inert solvents for use as wetting agents in the blending/granulating step include isopropanol, methylene chloride, dioxane, tetrahydrofuran, and acetone. These may be used singly or in admixture with each other. (Methanol and ethanol, at least when used as the only solvents, have been found to be detrimental to the biological activity of the preparation under the foregoing conditions used for granulation, i.e., these solvents tend to destroy the biological activity of the enzymes.) The preferred solvents for granulation were found to be isopropanol, methylene chloride and dioxane. The most preferred solvent is isopropanol. (See Table III.)

Proper wetting of the enzyme powder with the solvent, e.g., isopropanol, for the granulation and for the subsequent manufacturing operation is important to achieve, and is dependent on the solvent concentration. Overwetting results in poor segmentation in the extruder and stickiness in the marumerization steps. Overwetting produced similar results when the nonpareil seeds were used, i.e., the beads stuck to the coating pan and they formed multiplets or agglomerates.

The proper amount of isopropanol for granulation was found to be between about 600 and about 700 ml/kg of enzyme blend. Best results were obtained with 625 to 675 ml of isopropanol per kg of enzyme blend. In the nonpareil process, evaporation is relatively rapid due to high surface area, so that proper wetting is a matter of continued surveillance, with periodic addition of binder solution as needed.

I have also found that water must be meticulously avoided during any phase of the processing operation since the presence of water even in small amounts is detrimental to the biological activity of the enzymes. Therefore, it is also important that incidental moisture content resulting from normal processing of raw materials as well as the humidity of the air in the facility where the manufacturing of the enzyme composition is carried out to be kept as low as possible.

f. Enteric Coating

I have discovered that in order to obtain an enteric coating polymer having the necessary properties to survive gastric conditions for at least about 1 hour, preferably 2 hours, and readily disintegrate in the duodenum under neutral to alkaline pH, the enteric coating polymer must comprise at least about 3 to 3.5% by weight of the uncoated beads, whereas about 2.5 wt. % of enteric coating polymer (based on the weight of the uncoated tablets) is sufficient for the tablets. To assure adequate protection against gastric conditions, particularly in the case of tablets on which it is more difficult to obtain a uniform coating, the thickness of coating at the edges generally differing from that at the central portion, I prefer to use amounts of about 3 to about 8% w/w of enteric coating polymer. While greater amounts of enteric coating polymer could be used, there would be no advantage to exceeding about 10% by weight, as the thicker the coating, the slower the dissolution in the normal intestinal environment. The most preferred range of enteric coating polymer is between about 4.5 and 8% w/w for the beads; and between about 3.5 and about 5% for the tablets.

In one preferred method of carrying out the coating operation, separate solutions of 1%, 2% and 4% concentration are prepared by dissolving the enteric coating polymer in a suitable solvent, preferably a solvent pair such as chloroform; methanol or isopropanol:ethyl acetate (1:1 w/w). Then, starting with the most concentrated solution, the tablets or beads are sprayed in a coating pan under carefully controlled conditions, as determined by visual observation, until the desired film thickness, corresponding to the desired coating weight, is achieved. During the coating operation, it has been observed that rapid aggregation of the tablets or the beads into multiplets. This, however, could be prevented by lightly dusting Talc U.S.P. over the overwetted tablets or beads. Many suitable enteric coating compositions meeting the requirements of my invention, as well as suitable alternative enteric coating techniques, are well known in the art. Thus, for example, a single coating solution, with a solids content as high as 10%, has been found to be useful under appropriate conditions.

g. Dosage

The total amount of the composition required to be administered to an enzyme deficient patient will vary with the severity of the condition and the amount of food ingested. Generally, for a pancreatic enzyme deficient patient from about 0.8 to 1.5 gms. of the final pancreatic enzyme composition are administered with each meal. This amounts to about 2 about 3 capsules of small beads or tablets. In the presently preferred embodiment, each capsule comprises from about 0.425 to about 0.475 gms. of digestive enzyme composition, whether in bead or tablet form.

h. Discussion of Tables

Table I below illustrates the deficiencies of currently available enzyme containing products, which are ineffective or only partially effective to replace the missing enzymes in most pancreatic enzyme deficient patients. As can be seen from the comparative data in that table, most products on the market contain low levels of enzymes, they are especially deficient in lipase, and their enteric coatings fail adequately to protect the enzymes against gastric inactivation. By contrast, the compositions of the present invention are shown in Table I below to comprise known high potency enzymes in an effective binder system. Moreover, they have properly balanced enteric coatings whereby to avoid the inactivating effect of gastric acidity and pepsin. Therefore, the survival of the enzymes in active form is increased significantly so that their bioavailability in the duodenum is maximized.

Referring more particularly to Table I below, increased bioavailability is demonstrated for small tablets made of a composition of the present invention as described in Example 1. Thus, upon exposure to a simulated gastric environment for two hours, the biological activity of the preparations of this invention was well protected against gastric inactivation. Four of the nine commercially available enzyme compositions tested disintegrated within the first hour of exposure, and their enzymes were entirely inactivated. There were losses of at least 40% in the activity of at least one enzyme in three of the other five commercial compositions. After exposure to simulated intestinal juices (slightly alkaline), the tablets of the present invention disintegrated within about 15 minutes and released the enzymes in their active state. In contrast, three of the five remaining commercial preparations, which tested under identical conditions, failed to disintegrate in the intestinal environment within a reasonable time, and all had disintegration times greater than those of the tablets of Example 1. Reasonable time is defined as the time that is required for the food to be digested, transported and absorbed in the duodenum and upper intestine. The absorptive surfaces represent a segment of the upper intestine approximately 5 to 7 feet long. Transit of food through this segment of the intestine by peristalsis under normal physiological conditions usually requires 45 to 60 minutes. Therefore, any enteric coated preparation that requires a longer disintegration time than 60 minutes to release its enzyme content in this part of the upper intestine is considered to be defective, and hence to have little usefulness to the patient.

Bioassays of the intestinal juices showed that between 74% and 84% of the initial activities of the enzymes of the tablets of Example 1 were preserved during gastric exposure. By contrast, most of the commerical preparations had lost at least 50% of the initial activity of at least one of its enzymes. In fact, a comparison of the initial activities shown in Table I with the activities after 1 hour exposure to intestinal fluid (which followed the two-hour exposure to gastric fluid) shows that only the tablets of the present invention were able to maintain and deliver a high concentration of active enzymes of all three enzymes whose activities were tested, even though several of the commerical compositions showed initial enzyme activities of at least one of the enzymes comparable to that of the tablets of Example 1.

Table II shows the performance of beads prepared in accordance with Example 9 after one hour exposure to gastric fluid followed by exposure to intestinal fluid. Note that complete disintegration, with delivery of at least 95% of initial enzyme activity of each of the enzymes, took place within 20 minutes. Moreover, even after only 10 minutes exposure of the intestinal fluid, adequate delivery of active enzyme had already occurred (75.1% Protease; 85.5% Amylase; 100% Lipase).

Table III is self-explanatory and shows that isopropanol is a safe, fully compatible solvent for use with the enzymes in accordance with the present invention, whereas methanol has such poor compatibility that it is unsuitable. Acetone, chloroform and dioxane, while having some deleterious effect on enzyme activity, are also suitable, although less desirable than isopropanol.

Further experimentation with freshly aspirated human gastric duodenal juices revealed that the exogenously administered enzyme system of the present invention (tablets of Example 1) is compatible with human duodenal juices and stabilizes the patient's pancreatic enzymes against temperature inactivation (Tables IV and V). That is, the enteric coated enzyme tablets of Example 1 were resistant to gastric inactivation, and the enzymes released in the duodenum were biologically active and were compatible with the patient's enzyme system (Table IV). In addition, the exogenously administered enzyme system stabilized the patient's enzyme system against temperature inactivation (Table V). This unexpected benefit resulted in longer digestion and better utilization of foods; and separate studies showed that the polymers polyvinylpyrrolidone and cellulose acetate phthalate (used as binders) stabilized the enzymes against temperature denaturation and self-digestion. Most conventional preparations, however, have been found to be substantially inactivated when subjected to identical environmental conditions.

Referring to Table VI, disc gel electrophoretic studies of duodenal juices aspirated after the administration of the enteric coated digestive aid confirmed that the enzymes were released from the tablets and beads into the duodenum and that the released enzymes were biologically active. Thus, it can be seen that when the digestive enzyme compositions of this invention are employed, the biological activities of the enzymes are preserved and protected from gastric inactivation. Moreover, they are released in the duodenum within 5 to 30 minutes in their active state.

Lipase is dependent on co-lipase for enzyme activity. As shown in Tables VII and VIII, it has been discovered during the course of my investigation that the presence of co-lipase in the compositions of this invention activates and stabilizes the lipase of pancreatic patients (Table VIII). Our clinical studies have shown that many pancreatic patients, to some extent, are deficient in co-lipase, and that co-lipase, stabilizes lipase against bile salt (Na taurocholate) inactivation. (Compare Table VII with Table VIII.) In the absence of co-lipase, fat digestion is impaired. Therefore, an additional benefit of the preferred compositions of this invention is the availability and delivery of an essential cofactor (co-lipase) that is necessary for lipid digestion. The manufacturing procedure outlined above preserves the biological activity of co-lipase and the uniform enteric coating ensures that the co-lipase is delivered into the duodenum intact in its biologically active form.

j. Examples

The following specific examples are presented to further illustrate the compositions and methods of this invention, without thereby limiting the scope thereof. Unless otherwise indicated, all percentages are by weight.

EXAMPLE 1

| Phase 1 | Pancreatic enzyme powder (5 × N.F. Pancreatin) | 67.0% |
|---|---|---|
| | Polyvinylpyrrolidone | 1.3% |
| | Starch (Sta-Rx 1500) | 5.0% |
| | Sodium bicarbonate (anhydrous) | 20.0% |
| | Citric acid | 6.7% |
| | | 100.0% |
| | Solvent: Isopropanol (anhydrous) 700 ml/kg blend | |
| Phase 2 | (Enteric coating composition) | |
| | Chloroform | 66.4% |
| | Methanol (anhydrous) | 15.4% |
| | Cellulose acetate phthalate | 7.2% |
| | Talc #127 U.S.P. | 7.3% |
| | FD & #5 yellow | 1.0% |
| | Diethyl phthalate | 2.7% |
| | | 100.0% |

The phase 1 composition was granulated, extruded and either tableted or processed into beads under the following conditions. The enzyme powder was blended with polyvinylpyrrolidone, Starch 1500, sodium bicarbonate and citric acid in a Pony Mixer pan, with the slow addition of 700 ml/kg of isopropyl alcohol (anhydrous) for 9 to 15 minutes. The resulting blend was then segmented by means of a Stokes extruder, model EXKS-1, through openings of about 1 mm in diameter.

In preparing beads, the segmented particles were rounded off by means of a marumerizer into spherical particles. The marumerizer speed was 430 rpm. Time of marumerization was varied between 45 to 75 seconds. (Longer marumerization times are avoided as they were found to result in more compact, dense particles. This in turn resulted in longer disintegration times.) The resulting beads were about 10 - 12 mesh in size. After spheronization, the solvent was evaporated under controlled conditions of low humidity, i.e., 5 to 10% relative humidity, and temperature, i.e., about 35° C.

To prepare small tablets, another portion of segmented particles was dried in an oven at 35° C for approximately 40 to 48 hours. The dried granules were sized through a 14 mesh screen. The segments which passed through the screen were then compressed on a Stokes BB 2 tablet machine employing 3/16 deep cut tooling (or punches) to produce tablets about 3/16 (4.8 mm) in diameter and about 0.155 (4 mm) thickness. Machine speed was approximately 17 rpm.

The dried spherical granules or tablets were then coated with a pH sensitive enteric coating composition having the composition set forth above (Phase 2) in an appropriate coating pan, e.g., one available from the Manesty Co., employing approximately 0.45 liters of coating solution per kilogram of tablets and approximately 0.8 liters of coating solution per kilogram of beads, until the appropriate film thickness was achieved.

Additional examples of suitable Phase 1 compositions are set forth below in Examples 2 – 9, while Example 9 also contains an illustration of a suitable alternative Phase 2 enteric coating composition, particularly suitable for coating beads uniformly.

The Phase 1 compositions illustrated in Examples 2 through 8 are blended in a mixing apparatus with the indicated solvent and then extruded into segments by an extruder as described in Example 1, followed by processing into tablets or beads and enteric coating, also as described in Example 1.

EXAMPLE 2

| Phase 1 | Pancreatic enzymes (5 × N.F. Pancreatin) | 90.0% |
|---|---|---|
| | Polyvinylpyrrolidone K30 | 3.0% |
| | Avicel (crystalline cellulose having a molecular weight in the range of 30,000 to 50,000) | 7.0% |
| | | 100.0% |
| | Solvent: Isopropanol 675 mg/kg blend | |

EXAMPLE 3

| Phase 1 | Pancreatic enzymes (5 × N.F. Pancreatin) | 89.0% |
|---|---|---|
| | Polyvinylpyrrolidone K30 | 4.5% |
| | Sta-Rx (corn starch) | 6.5% |
| | | 100.0% |
| | Solvent: Isopropanol 625 ml/kg blend | |

EXAMPLE 4

| Phase 1 | Pancreatic enzymes (5 × N.F. Pancreatin) | 89.0% |
|---|---|---|
| | Cellulose acetate phthalate | 4.5% |
| | Sta-Rx (corn starch) | 6.5% |
| | | 100.0% |

Solvent: Acetone - Isopropanol (1:3) 700 ml/kg blend

EXAMPLE 5

| Phase 1 | Pancreatic enzymes (5 × N.F. Pancreatin) | 90.0% |
|---|---|---|
| | Polyvinylpyrrolidone K30 | 2.0% |
| | Methocel 65 HG | 1.0% |
| | Sodium carbonate (anhydrous) | 4.0% |
| | Citric Acid (anhydrous) | 3.0% |
| | | 100.0% |
| | Solvent: Isopropanol 650–675 ml/kg blend | |

EXAMPLE 6

| Phase 1 | Pancreatic enzymes (5 × N.F. Pancreatin) | 90.0% |
|---|---|---|
| | methocel 65 HG | 1.0% |
| | Sodium carbonate (anhydrous) | 4.0% |
| | Citric acid (anhydrous) | 3.0% |
| | Polyvinylpyrrolidone K-30 | 2.0% |
| | | 100.0% |

Solvent:

-continued
EXAMPLE 6
Isopropanol 650–700 ml/kg blend

The citric acid (30 gm) and the polyvinylpyrrolidone (20 gm) are separately dissolved in isopropanol (500 ml) before the addition to the above blend.

EXAMPLE 7
| Phase 1 | Lactase derived from yeast | 83.0% |
|---|---|---|
| | Methocel 65 HG | 2.0% |
| | Sta-Rx (modified corn starch) | 15.0% |
| | | 100.0% |

Solvent:
Isopropanol 675–725 ml/kg blend

EXAMPLE 8
| Phase 1 | Enzyme blend* | 87.02% |
|---|---|---|
| | Methocel 65 HG | 2.0% |
| | Polyvinylpyrrolidone K-30 | 4.0% |
| | Sodium carbonate or bicarbonate | 4.0% |
| | Citric acid (anhydrous) | 3.0% |
| | | 100.0% |

Solvent:
Isopropanol 650–750 ml/kg blend

*Enzyme blend composition: Papain, Ficin, Bromelain (enzymes from plant); Lipase, Cellulase, Protease, Amylase and Lactase (enzymes from microorganisms).

EXAMPLE 9 Beads by Nonpareil Process
| Phase 1 | Pancreatic enzymes (5 × N.F. Pancreatin) | 80.0% |
|---|---|---|
| | Polyvinylpyrrolidone K-30 | 6.5% |
| | Primojel (modified potato starch) | 3.5% |
| | Nonpareil seeds (sugar seeds 20–30 mesh size) | 10.0% |
| | | 100.0% |

Solvent:
Isopropanol 675–725 ml/kg blend

The composition of Example 9 (Phase 1) was processed in accordance with the nonpareil process described above. The enteric coating was performed as described above using the Phase 2 enteric coating composition set forth below, to give a uniform coating weighing about 5.5% by weight of the final bead.

| Phase 2 | (Enteric coating composition) | |
|---|---|---|
| | Cellulose acetate phthalate | 8.0% |
| | Diethyl phthalate | 2.0% |
| | Ethyl acetate | 45.0% |
| | Isopropanol | 45.0% |
| | | 100.0% |

The resulting beads were screened, giving a yield of about 90% by weight of beads in the 10–12 mesh size range.

TABLE I
COMPARATIVE EVALUATION OF COMMERCIAL DIGESTIVE ENZYME COMPOSITIONS WITH TABLET PRODUCT OF PRESENT INVENTION

| | PRODUCT | PROTEASE (μ/gm) | AMYLASE (μ/gm) | LIPASE (μ/gm) | DISINTEGRATION TIME (Minutes) |
|---|---|---|---|---|---|
| INITIAL ACTIVITY (μ/gm) | Panteric granules | 186,200 | 29,600 | 7,970 | |
| | Pancrex V | 87,000 | 7,000 | 260 | |
| | Cotazyme | 130,000 | 23,000 | 9,600 | |
| | Entozyme | 19,700 | 1,800 | 55 | |
| | Donnazyme | 14,700 | 2,160 | 915 | |
| | Phazyme | 13,600 | 2,280 | 630 | |
| | Panteric | 50,000 | 9,500 | 935 | |
| | Viokase | 238,000 | 27,000 | 10,800 | |
| | Dactilase | 37,650 | 6,500 | 880 | |
| | Product of Example 1 * | 211,000 | 29,600 | 11,400 | |
| ACTIVITY AFTER EXPOSURE TO GASTRIC FLUID, pH 1.8, FOR 2 Hrs. | Pantoric Granules | NIL | NIL | NIL | 25 |
| | Pancrex V | 72,000 | 6,500 | 250 | N ** |
| | Cotazyme | NIL | NIL | NIL | R *** |
| | Entozyme | 15,075 | 2,640 | 680 | N |
| | Donnazyme | 8,850 | 1,440 | 1,030 | N |
| | Phazyme | 4,100 | 440 | 370 | N |
| | Panteric | 40,000 | 7,000 | 410 | N |
| | Viokase | NIL | NIL | NIL | 5 |
| | Dactilase | NIL | NIL | NIL | 60 |
| | Product of Example 1 | 177,000 | 24,900 | 8,425 | N |
| ACTIVITY AFTER EXPOSURE TO INTESTINAL FLUID, pH 7.5, FOR 1 Hr. | Panteric Granules | NIL | NIL | NIL | — **** |
| | Pancrex V | 62,000 | 5,000 | 130 | 60 |
| | Cotazyme | NIL | NIL | NIL | — |
| | Entozyme | 13,550 | 1,600 | 390 | 20 |
| | Donnazyme | 5,780 | 2,030 | 400 | 25 |
| | Phazyme | 8,375 | 725 | 110 | 40 |
| | Panteric | 40,000 | 6,200 | 370 | 150 |
| | Viokase | NIL | NIL | NIL | — |
| | Dactilase | NIL | NIL | NIL | — |
| | Product of Example 1 | 151,000 | 21,200 | 7,100 | 15 |

* Example I, Phase I and II combined in tablet form. Tablet size: 3/16" diameter and 0.155" thickness.
** N = No disintegration
*** R = Rapid disintegration
**** — = Not determined since disintegration had already occurred in gastric fluid.

TABLE II
RATE OF ENZYME RELEASE FROM BEADS* INTO DUODENAL JUICE AFTER EXPOSURE TO GASTRIC JUICE

| | PROTEASE | AMYLASE | LIPASE |
|---|---|---|---|
| 1. Initial Activity (μ/gm) | 123,060 (100%) | 41,112 (100%) | 11,773 (100%) |
| 2. Exposure to simulated gastric fluid for one hr. followed by exposure to simulated intestinal fluid, pH 7.5 at 37° C. | | | |

TABLE II-continued
RATE OF ENZYME RELEASE FROM BEADS* INTO DUODENAL JUICE AFTER EXPOSURE TO GASTRIC JUICE

|  | PROTEASE | AMYLASE | LIPASE |
|---|---|---|---|
| 5 min. | 25,963 (21.1%) | 8,836 (21.5%) | 2,527 (21.5%) |
| 10 min. | 92,445 (75.1%) | 35,135 (85.5%) | 13,196 (100%) |
| 15 min. | 116,717 (94.8%) | 38,137 (92.8%) | 13,118 (100%) |
| 20 min. | 118,023 (96.0%) | 39,411 (95.9%) | 13,040 (100%) |

*Example 9, Phases I and II, in bead form.
Bead size: 10–12 mesh.
Enteric coating = 5.5% w/w.

TABLE III
COMPATIBILITY OF THE 5 × N.F. PANCREATIN ENZYMES WITH SOLVENTS

|  | PROTEASE | AMYLASE | LIPASE |
|---|---|---|---|
| Untreated Control | 100% | 100% | 100% |
| Methanol, Reagent Grade | 16% | 10% | 45% |
| Isopropanol, N.F. | 100% | 100% | 100% |
| Acetone, Reagent Grade | 83% | 75% | 94% |
| Chloroform, Reagent Grade | 96% | 81% | 100% |
| Dioxane, Reagent Grade | 94% | 76% | 100% |

*Remaining enzymatic activities after granulation for 4 hours with the respective solvents at 25° C.

TABLE IV
COMATIBILITY OF THE TABLETS OF EXAMPLE I WITH HUMAN DUODENAL FLUIDS AT 10° C.

|  |  | LIPASE | TRYPSIN | CHYMOTRYPSIN | AMYLASE | PROTEASE | RN-ase |
|---|---|---|---|---|---|---|---|
| 1. | Human Duodenal Fluid | 91.8 | 212.7 | 178.5 | 5.9 | 23.8 | 16.9 |
| 2. | Digestive Enzyme Tablet of Example I | 204 | 170 | 170 | 23.4 | 33.7 | 308 |
| 3. | Digestive Enzyme Tablet of Example I Exposed to Human Duodenal Fluid for one Hr. | 323 | 368.6 | 286 | 39.3 | 58.4 | 326.3 |

NOTE: Comparison of column 3 with the sum of columns 1 and 2 clearly show that the digestive enzymes in the tablets of Example 1 are compatible with the human pancreatic enzymes (duodenal juice) and the biological activities are complimentary to each other.

TABLE V
TEMPERATURE STABILITY OF THE TABLETS OF EXAMPLE I IN HUMAN GASTRIC AND INTESTINAL FLUIDS

|  |  | LIPASE | TRYPSIN | CHYMOTRYPSIN | AMYLASE | PROTEASE |
|---|---|---|---|---|---|---|
| 1. | Hormone* Stimulated Duodenal Fluid | 383 | 680 | 595 | 7.33 | 6.42 |
| 2. | Hormone Stimulated Duodenal Fluid incubated at 37° C. for 40 min. | 5.1 | 57.1 | 59.5 | 7.33 | 9.53 |
| 3. | Digestive Enzyme Tablet of Example I in Phosphate Buffer, pH 7.4 | 204 | 170 | 170 | 23.4 | 33.7 |
| 4. | Digestive Enzyme Tablet of Example I in Phosphate Buffer, pH 7.4 incubated at 37° C. for 40 min. | 141 | 117 | 117 | 17.1 | 29.0 |
| 5. | Digestive Enzyme Tablet of Example I Exposed to Human Gastric Fluid (1 Hr.) followed by Duodenal Fluid at 37° C. for 40 min. | 478 | 382 | 306 | 45.4 | 62.4 |
| 6. | Sum of activities in Columns 2 and 4 | 146.1 | 174.1 | 176.5 | 24.43 | 38.53 |

NOTE: Inspection of columns 1 vs. 2 and 3 vs. 4 show that exposure of the respective enzyme solutions to elevated temperatures is detrimental to the biological activities of the enzymes. If one sums up the activities of column 2 with 4, column 6 is obtained. Comparison of columns 5 vs. 6 clearly show that the composition of the Tablets of Example I stabilizes the biological activities of the duodenal juice against temperature inactivation.
*Secretin and Cholecystokinin - Available for investigational use in prepared ampules together with printed instructions for use from:GIH Research Unit, Chemistry Department, Karolinska Institutet, S-104 01 Stockholm 60, Sweden.

TABLE VI
DISTINTEGRATION OF THE EXOGENOUSLY ADMINISTERED TABLETS OF EXAMPLE I IN THE HUMAN DUODENUM

|  |  | LIPASE | TRYPSIN | CHYMOTRYPSIN | AMYLASE | PROTEASE | PROTEIN |
|---|---|---|---|---|---|---|---|
| 1. | Duodenal Aspirate 30 min. after tube insertion | 0 | 0 | 0 | 10 | 0 | 144 |
| 2. | 30 min. after administration of Digestive Enzyme Tablets of Example I | 0 | 0 | 0 | 6 | 0 | 25 |
| 3. | 60 min. after Digestive Enzyme Tablets of Example I | 1,521 | 4,973 | 4,973 | 16,120 | 2,178 | 426 |

NOTE: The appearance of biological activity after 60 min. (3) is proof that the enzymes are released from the Tablets of Example I in the duodenum, within 5–30 minutes after leaving the stomach.

TABLE VII
CO-LIPASE DEFICIENCY IN HUMAN DUODENAL JUICE

| SUBJECT | WITH TAUROCHOLATE* | WITHOUT TAUROCHOLATE |
|---|---|---|
| R.P. | 382 | 17,959 |
| H.M. | 120 | 160 |
| E.R. | 5,663 | 43,250 |
| E.R. | 51 | 17,803 |
| J.P. | 2,446 | 14.693 |
| J.C. | 0 | 3,289 |

*Conc. of taurocholate 0.2 mg/ml
NOTE: Na-taurocholate inactivates lipase in the absence of co-lipase.

TABLE VIII
ACTIVATION OF CO-LIPASE DEFICIENT HUMAN LIPASE BY THE ADDITION OF THE DIGESTIVE ENZYME TABLETS OF EXAMPLE I

| | WITH TAUROCHOLATE | WITHOUT TAUROCHOLATE |
|---|---|---|
| 1. Human Duodenal Aspirate | 92 | 271 |
| 2. Digestive Enzyme Tablets of Example I | 204 | 102 |
| 3. Digestive Enzyme Tablets of Example I Dissolved in Human Duodenal Aspirate | 323 | 336 |

NOTE: The increased activity in the presence of taurocholate (3) shows that the free co-lipase in the Digestive Enzyme Tablets of Example I activates and stabilizes the co-lipase deficient human lipase.

What is claimed:

1. In a process for preparing a digestive enzyme composition for treating enzyme deficient mammals, said composition comprising (a) a concentrate of an enzyme from the group consisting of the pancreatic proteases, lipases, nucleases and amylase, the plant-derived digestive enzymes and the digestive enzymes derived from microbial sources in (b) a binder system comprising (i) at least about 0.5 wt. % (based on the weight of the binder system plus enzymes) of a binder selected from the group consisting of polyvinylpyrrolidone, microcrystalline cellulose, cellulose acetate phthalate, methylcellulose and alginic acid, and (ii) from zero to about 10 wt. % (based on the weight of the binder system plus enzymes) of a stabilizer selected from the group consisting of calcium carbonate, polyvinylpyrrolidone, cellulose acetate phthalate, methylcellulose, starch and modified starches and alginic acid; and (c) from about 0.1% to about 30 wt. %, based on the weight of the total composite (enzyme plus binder system plus disintegrant), of a disintegrant selected from the group consisting of citric acid, sodium carbonate, sodium bicarbonate, calcium carbonate, starch and modified starches, microcrystalline cellulose, and alginic acid; said process including the steps of blending said enzyme with said binder system and said disintegrant to form a composite and thereafter coating said enzyme/binder system/disintegrant composite with a non-porous, pharmaceutically acceptable enteric coating which is insoluble in the pH range of from about 1.5 to about 5 but is soluble in the pH range of from about 6 to about 9, the improvement consisting of carrying out said process while avoiding the presence of water and said blending step being performed in the presence of a single liquid phase comprising an inert organic enzyme-compatible solvent.

2. The process of claim 1 wherein said enzyme is selected from the group consisting of Trypsin, Chymotrypsin, Chymotrypsin B, Pancreatopeptidase, Carboxypeptidase A, Carboxypeptidase B, Glycerol ester hydrolase, Phospholipase $A_2$, Sterol ester hydrolase, Ribonuclease, Deoxyribonuclease, $\alpha$-Amylase, Papain, Chymopapain, Bromelain, Ficin, $\beta$-Amylase, Cellulase, $\beta$-Galactosidase, Subtilopeptidase A, and Aspergillopeptidase A.

3. The process of claim 1 wherein said enzyme concentrate comprises an enzyme mixture, each milligram of which contains at least about 75 N.F. units of protease activity, at least about 75 N.F. units of amylase activity, at least about 10 N.F. units of lipase activity, and an effective amount of co-lipase.

4. The process of claim 3 wherein said enzyme mixture further contains at least about 5 International Units of ribonuclease activity per milligram.

5. The process of claim 1 wherein said stabilizer is present in an amount of from about 0.1% to about 10% by weight.

6. The process of claim 1 wherein said binder is present in an amount of from about 1% to about 5% by weight.

7. The process of claim 1 wherein said disintegrant is present in an amount of from about 2% to about 15% by weight.

8. The process of claim 1 wherein said binder is methyl cellulose.

9. The process of claim 1 wherein said binder is polyvinylpyrrolidone, which also acts as said stabilizer.

10. The process of claim 1 wherein said enteric coating is present in an amount of from about 2.5% to about 10% by weight of the entire composition.

11. The process of claim 1 wherein said enteric coating comprises cellulose acetate phthalate and diethyl phthalate.

12. The process of claim 1 wherein said binder and said disintegrant are first dissolved in said solvent and the resulting solution is then slowly added to said enzyme mixture.

13. The process of claim 1 wherein said solvent is isopropanol.

14. The process of claim 1, which includes the steps of granulating the resulting blend, extruding it into segments, screening the segments and subsequently tableting the resulting granules at a sufficiently low compression pressure that the temperature during compression is maintained in the range of from about 15° to about 30° C.

15. The process of claim 1 wherein said solvent is employed in an amount of from about 600 to about 700 ml. per kg. of blend of enzyme mixture plus binder plus disintegrant.

16. The process of claim 1 wherein said blend is granulated, extruded through a screen with uniform openings having a diameter in the range of between about 0.5 mm and about 2 mm, and thereafter formed into spheres having a size in the range of between about 8 and about 14 mesh by processing said extruded pellets on a Marumerizer for from about 30 seconds to about 75 seconds.

17. The process of claim 16 wherein said Marumerization is performed at a temperature not greater than about 20° C.

18. The process of claim 1 wherein said blend is prepared by combining said disintegrant and said enzyme mixture in a suitable apparatus to form a uniform dry blend; said binder is separately dissolved in said solvent, and the composition is formed into spheres having a diameter in the range of from about 8 to about 14 mesh by dusting said dry blend over nonpareil seeds tumbling and flowing in a coating pan, said seeds having been wetted with said binder solution, with periodic addition of said solvent to maintain the particles in a wetted but free-flowing state, until the seeds have been built to uniform spherical particles having diameters predominantly in said range of from about 8 to about 14 mesh.

19. The process of claim 18 wherein said dusting operation is performed until said diameters of said spheres are predominantly in the range of from about 10 to about 12 mesh.

20. The process of claim 1 which further comprises applying an enteric coating to said tablets or spheres by spraying solutions of progressively lower concentrations of an enteric coating composition onto said tablets or spheres in a coating pan until the desired coating thickness is achieved.

21. The process of claim 20 wherein said enteric coating solution comprises cellulose acetate phthalate and diethyl phthalate in at least one solvent selected from the group consisting of acetone, methyl ethyl ketone, diacetone alcohol, ethylene glycol monoacetate, ethanol, chloroform, methanol, isopropanol, ethyl acetate, methylene chloride and benzene.

22. The process of claim 21 wherein said solvent is a mixture of equal parts by volume of chloroform and methanol, or of isopropanol and ethylacetate.

23. A digestive enzyme composition prepared by the process of claim 1.

24. A digestive enzyme composition prepared by the process of claim 14.

25. A digestive enzyme composition prepared by the process of claim 16.

26. A digestive enzyme composition prepared by the process of claim 18.

27. A method for treating digestive enzyme deficiency in mammals comprising feeding the mammal with each meal an effective amount of the composition of claim 25.

28. The method of claim 27, wherein from about 0.8 to about 1.5 grams of said composition are fed with each meal.

29. The method of claim 28 wherein said composition is in the form of spheres of a size in the range of from about 8 to about 14 mesh.

30. The method of claim 1 wherein said inert organic enzyme-compatible solvent is a member selected from the group consisting of isopropanol, methylene chloride, dioxane, tetrahydrofuran and acetone.

* * * * *

UNITED STATES PATENT AND TRADEMARK OFFICE
CERTIFICATE OF CORRECTION

PATENT NO. : 4,079,125

DATED : March 14, 1978

INVENTOR(S) : Tibor Sipos

It is certified that error appears in the above-identified patent and that said Letters Patent are hereby corrected as shown below:

Col. 1, line 43: change "reponse" to -- response --.
Col. 1, line 44: change "exzymes" to -- enzymes --.
Col. 3, line 52: change "Vol. VIII" to -- Vol. XIII --.
Col. 5, line 24: change "E,C, 3,4,4,5; Chymotrypsin B, E.C. 3,4,4,6;" to -- E,C, 3.4.4.5; Chymotrypsin B, E.C. 3.4.4.6; --.
Col. 6, line 2: change "0.5" to -- 0.1 -- to conform with Claim 1.
Col. 8, line 66: after "rapid" insert -- application of the coating solution results in clumping and --.
Col. 9, line 16: change "2 about" to -- 2 to about --.
Col. 9, line 56: change "which tested" to -- when tested --.
Col. 10, line 26: change "exposure of" to -- exposure to --.
Col. 11, line 38: change "FD & #5" to -- FD & C #5 --.
Col. 11, lines 67 and 68: after "3/16" (in each instance) insert -- " (inch) --.
Col. 12, line 1: after "0.155" insert -- " (inch) --.
Col. 13, line 19: change "87.02% to -- 87.0% --.
Col. 14, "Table I, under heading "Lipase (u/gm)" (fourth and fifth entries:) change "55" to -- 975 --.
change "915" to -- 935 --.

UNITED STATES PATENT AND TRADEMARK OFFICE
CERTIFICATE OF CORRECTION

PATENT NO. : 4,079,125

DATED : March 14, 1978

INVENTOR(S) : Tibor Sipos

It is certified that error appears in the above-identified patent and that said Letters Patent are hereby corrected as shown below:

Col. 14, Same Table: under heading "Disintegration Time (Minutes)" (eighth entry) change "5" to -- 55 --.

Col. 15, first line of heading of Table IV: change "COMATIBILITY" to -- COMPATIBILITY --.

Signed and Sealed this

Seventeenth Day of October 1978

[SEAL]

Attest:

RUTH C. MASON
Attesting Officer

DONALD W. BANNER
Commissioner of Patents and Trademarks